US006254878B1

(12) United States Patent
Bednarek et al.

(10) Patent No.: US 6,254,878 B1
(45) Date of Patent: Jul. 3, 2001

(54) NAIL POLISH COMPOSITIONS CONTAINING ACRYLIC POLYMERS

(75) Inventors: Milan Bohuslav Bednarek; Christopher Scopazzi, both of Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/346,374

(22) Filed: Jul. 1, 1999

(51) Int. Cl.[7] .............................. A61K 6/00; A61K 7/00; A61K 7/04
(52) U.S. Cl. ............................... 424/401; 424/61
(58) Field of Search ........................ 424/61, 401

(56) References Cited

U.S. PATENT DOCUMENTS

| 4,747,419 | 5/1988 | Flynn et al. ................. 132/73 |
| 4,906,684 | 3/1990 | Say ................................ 524/548 |
| 5,057,312 | 10/1991 | Langla et al. .................. 424/81 |
| 5,266,322 | 11/1993 | Myers et al. .................. 424/401 |
| 5,380,520 | 1/1995 | Dobbs ............................ 424/61 |
| 5,681,550 | 10/1997 | Rubino ........................... 424/61 |
| 5,716,603 | * 2/1998 | Chen et al. ..................... 424/61 |
| 5,798,426 | 8/1998 | Anton et al. ................... 526/318.41 |
| 5,851,517 | 12/1998 | Mougin et al. ................. 424/78.02 |
| 5,863,523 | 1/1999 | Socci et al. .................... 424/61 |
| 5,882,635 | 3/1999 | Ramin et al. ................... 424/61 |

FOREIGN PATENT DOCUMENTS 0 626 397 A1   11/1994   (EP) .

* cited by examiner

*Primary Examiner*—Thurman K. Page
*Assistant Examiner*—S. Howard
(74) *Attorney, Agent, or Firm*—Joseph A. Tessari

(57) ABSTRACT

Colored and clear nail polish compositions comprise a solvent system having no more than 30 weight % water, a film forming acrylic binder prepared from (meth)acrylic monomers and stirene and which further contain specific adhesion promoting monomers or monomer combinations selected from (1) anhydride, anhydride plus acid, anhydride plus ureido, anhydride plus beta-diketone; (2) acid plus hydroxy; and (3) ureido, ureido plus acid, or ureido plus beta-diketone have properties equal to or better than commercially available nail polish compositions and permit the formulation of all acrylic pigmented nail polish compositions.

6 Claims, No Drawings

NAIL POLISH COMPOSITIONS CONTAINING ACRYLIC POLYMERS

BACKGROUND OF THE INVENTION

This invention relates to acrylic nail polish compositions and, more specifically, to nail polish compositions containing acrylic polymeric film forming binders, acrylic polymeric pigment dispersant, or both acrylic binders and acrylic dispersants.

All currently manufactured nail polish products contain nitrates of cellulose, either as a pigment dispersant or as a film forming binder. These nitrates of cellulose provide very good film forming properties when properly plasticized, and are relatively inexpensive materials. However, nitrocellulose materials present a severe safety hazard in their manufacture, transportation, and storage. While newer nail polish products have begun replacing the nitrocellulose binders with other types of film-forming polymers (e.g., acrylic resins, polyester resins), nitrocellulose is still used as a pigment dispersant in the colored nail polish grades.

In the abstract, the concept of formulating a nail polish composition with acrylic dispersants and acrylic binders might seem simple. In practice, however, it has proven far more difficult than one might imagine. Acrylic monomers are toxic materials and care needs to be taken in formulating cosmetics or other products were ingestion might be a significant issue. In addition developing acrylic dispersants and binders that are compatible with those solvents to form stable dispersions is a challenge.

Furthermore, the acrylic binders and dispersants need to be compatible with one another (as well as the solvents) in the same composition. Compatibility means that the nail polish composition must be a single phase, homogeneous composition that is free of grit and lumps and must produce a smooth coating of uniform color and appearance that is clear and not cloudy. Finally, the commercial success of a nail polishes is determined by factors such as hardness, gloss, resistance to cracking, fading, chipping, peeling, drying time, and resistance to water, soaps, cleaning solutions and lotions. Thus, if any acrylic nail polish composition must at least be able to match a nitrocellulose based composition in these properties.

SUMMARY OF THE INVENTION

In one aspect, the present invention provides a nail polish composition comprising:

a) a solvent system comprising no more than 30% water by weight, based on the weight of the solvent system; and b) a binder comprising an acrylic copolymer of monomers selected from the group consisting of (meth)acrylic acid, esters of (meth)acrylic acid, and stirene; wherein said binder further contains adhesion promoting monomers selected from the group consisting of (1) anhydride monomers, anhydride monomers with acid monomers, anhydride monomers in combination with ureido monomers, and anhydride monomers with beta-diketone monomers; (2) acid monomers in combination with hydroxy monomers; (3) ureido monomers, ureido monomers in combination with beta-diketone monomers, and ureido monomers in combination with acid monomers.

In another aspect, the invention provides a nail polish composition comprising:

a) a solvent system comprising no more than 30% water by weight based on the weight of the solvent system;

b) a pigment;

c) a polymeric dispersant comprising an acrylic polymer comprising monomers selected from the group consisting of (meth)acrylic acid, esters of (meth)acrylic acid, and stirene; and d) a binder.

In a preferred aspect, the present invention provides a nitrocellulose-free nail polish composition wherein both the polymeric dispersant and the binder comprise acrylic polymers.

In a most preferred aspect, the present invention provides a nitrocellulose-free nail polish composition wherein both the polymeric dispersant and the binder comprise acrylic polymers and wherein the dispersant and the binder are prepared from the same monomers.

DETAILED DESCRIPTION

The nail polish compositions of this invention are those containing an acrylic polymer. The polymer may be in the form of a pigment dispersant or a film forming binder. The present nail polish compositions have properties (hardness, gloss, dry time, etc.) equal to better than commercial nail polish compositions that contain nitrates of cellulose, either as the dispersant and/or as the binder. The nail polish compositions of this invention include both colored nail polishes and clear coat nail polishes. The essential difference between the colored and clear nail polish compositions is that the colored nail polishes contain a pigment and a dispersant.

The nail polish compositions of this invention are those containing acrylic polymers, either as the film-forming binder or the pigment dispersant, but preferably as both. It is preferred for the nail polish compositions to be free of nitrocellulose and most preferred to have the composition contain an acrylic dispersant and an acrylic binder. However, it is understood that nail polish compositions of this invention may contain cellulosic esters, such as nitrocellulose, so long as either the dispersant (if present) or the polymer binder is an acrylic polymer as further defined herein. In other words, the present invention is intended to encompass those nail polish compositions containing a nitrocellulose dispersant in combination with an acrylic polymer binder (as defined herein) as well as nail polish compositions containing an acrylic polymer dispersant in combination with a nitrocellulose binder.

Certain terms are used throughout this specification that should be clarified to ensure a complete understanding of the disclosure. The terms "(meth)acrylic" and "(meth)acrylate" are used to refer to both the methylated and non-methylated forms of acrylic acid or acrylate monomers. The term "acrylic polymer" means polymers made from (meth)acrylic acid and/or (meth)acrylate monomers, alone or in combination with other (i.e., non-acrylic) monomers as more particularly defined herein.

The clear coat nail polish compositions of this invention contain two essential ingredients: the solvent system and the film forming acrylic polymer binder. The colored nail polish compositions of this invention contain four essential ingredients: solvent system, pigment, pigment dispersant (preferably an acrylic polymer) and a binder (preferably an acrylic polymer).

Solvent System

The nail polish compositions of this invention are solvent based, meaning that the liquid portion of the nail polish (i.e., the solvent system) comprises at least one organic non-aqueous solvent. It is not to advantage for water to be present in the nail polish compositions, so the presence of water in the solvent system is to be avoided. However, in some instances water might be present in small amounts as a by-product of ingredients used in the nail polish composition. For example, water may be introduced as an impurity in solvents or other components of the nail polish, or it may be introduced through the use of pigments supplied as a water-wet presscake.

Accordingly, while not preferred, the solvent system may comprise from 0–30% water by weight, based on the weight of the solvent system. For nail polish compositions comprising a high weight percent of the solvent system, the water content would be at the lower end of this range. Conversely, the solvent system can comprise a higher percentage of water in compositions where the solvent system comprises a small percent of the overall weight of the nail polish composition.

Suitable non-aqueous solvents include aliphatic or aromatic ketones such as acetone, diacetone alcohol, dihydroxyacetone, ethyl butyl valerolactone, methyl ethyl ketone; aliphatic or aromatic alcohols such as methanol, propanol, benzyl alcohol, butoxyethanol, butoxypropanol, butyl alcohol, 3-methyl-3-methoxy-butanol, t-butyl alcohol, butylene glycol, diethylene glycol, abietyl alcohol, propylene carbonate, hexyl alcohol, isopropanol; glycol ethers; esters such as butyl acetate, ethyl acetate, methyl acetate, propyl acetate, amyl acetate, alkanes for example, pentane, cyclopentane, hexane, heptane, cyclohexane, cyclic ethers for example, tetrahydrofuran and 1,4-dioxane, cellosolve, butyl cellosolve acetate, cellosolve acetate, methyl cellosolve acetate, butyl cellosolve, ethyl cellosolve, phenylated solvents for example, xylene, esters of acetic acid for example, methyl acetate, ethyl acetate, n-butyl acetate, and chlorinated hydrocarbons for example, methylene chloride, chloroform and methylchloroform. It is also contemplated that toluene, if desired, can be included as a solvent or diluent for use in a nail polish composition of the present invention. The aforementioned solvents can be used alone or in mixtures thereof.

The solvent system can comprise 20–95% by weight of the total nail polish composition, preferably 20 to 80% by weight, and more preferably 20 to 70% by weight.

Pigments

In color nail polish compositions according to the present invention, one or more pigments are added. Pigments are added to the composition to provide cosmetically acceptable shades and to pacify the films. Pigments for use in the present invention may include any of those pigments which are generally known for use in nail enamel compositions. For example, these pigments can include cosmetic grade or purified titanium dioxide, yellow, brown and red iron oxides, bismuth oxychloride, iron blue, iron black, mica particles, ultramarine blue, D&C and FD&C colors (e.g., D&C Reds #5, #6, #7, #10, #11, #12, #13 and #34), chromide oxide greens, carbon black and lampblack. Other pigments which may be used in compositions according to the present invention may include the Lake pigments, for example, D&C Red #6 barium Lake and D&C Red #7 calcium Lake, and the like. The pigments may be treated or coated with agents which modify the surface properties such as silicones. Examples of silicone treated pigments which can be used in the compositions of the invention are set forth in U.S. Pat. No. 4,832,944, which is hereby incorporated by reference.

In addition to the above named pigments, there may also be included titanated micas, polyethylene terephthalates and pearl essence which is a suspension of crystalline guanine in nitrocellulose and solvents, as well as other additives which will affect the appearance of the pigment.

Although the amount of pigment in the compositions of the present invention will vary as a function of the type of pigment and other components included in the composition, in general, pigments can be included in the amount of 0.1–30% by weight of the total composition, and preferably 0.5–20%, more preferably 1–15% and most preferably 1–8%.

Dispersants

Dispersants useful in the nail polish compositions of this invention include acrylic polymers, non-acrylic polymers, and thixotropic agents. The function of the dispersant is to maintain a homogeneous suspension of pigment particles in the nail polish composition. Acrylic polymer dispersants are particularly preferred.

Thixotropic agent may be employed to enhance the suspension of the pigments in the other components of the composition. Although a number of thixotropic agents which are generally used in conventional nail enamel compositions may be used to produce compositions according to the present invention, preferred thixotropic agents include the thixotropic clays (e.g., montmorillonite minerals), especially stearalkonium hectorite, stearalkonium bentonite and mixtures thereof, attapulgite, bentones, and the like. The thixotropic agent is present in the compositions of the present invention in amounts sufficient to produce a gel, preferably a colloidal gel. In general, the thixotropic agent is included in the amount ranging from 0.1–15%, preferably 0.5 to 3% by weight, and most preferably in the amount ranging from about 0.7 to 1.5% by weight.

Non-acrylic polymeric dispersants suitable for use in the inventive nail polish compositions include saccharide based polymers, polyesters, alkyd resins, polyamides, cellulosic polymers (e.g., nitrocellulose), sulfonated naphthalenes, vinyl polymers, formaldehyde condensates, polyurethanes, substituted pyrrolidone polymers, polypropylene oxides, silicone polymers and copolymers, toluene sulfonamide-formaldehyde condensates (for example Monsanto's SAN-TOLITE MHP), ethyl cellulose, dimer acid based polyamide resin (Henkel's Versamide 940) and polymeric esterified pentaerythritol (Hercules' Herco-Flex 900).

Acrylic polymer dispersants are preferred for use in the nail polish compositions of this invention. Such dispersants are prepared from (meth)acrylic acid monomers and/or esters of (meth)acrylic acid, either alone or copolymerized with stirene and/or anhydride monomers.

The structure of the acrylic polymer dispersants is not critical. Accordingly, the dispersants can have a random, block or branched (e.g., graft) structure and can be prepared by any conventional process used to prepare polymers of the desired structure. For example, random polymers may conveniently be prepared by a conventional solution polymerization processes in which the monomers, solvent and polymerization initiator are charged over a 1–24 hour period of time, preferably 2–8 hours, into a conventional polymerization reactor in which the constituents are heated to about 60–175° C., preferably 80–100° C.

Typical polymerization initiators that are used in the process are as follows: azo type initiators such as azo-bis-isobutyronitrile, 1,1'-azo-bis(cyanocyclohexane), peroxy acetates such as t-butyl peracetate; peroxides such as di-t-butyl peroxide, benzoates such as t-butyl perbenzoates, octoates such as t-butyl peroctoate and the like.

Typical solvents that can be used are ketones such as methyl amyl ketone, methyl isobutyl ketone, methyl ethyl ketone, aromatic hydrocarbons such as toluene and xylene, alcohols such as propanol, methoxy propanol and butanol, alkylene carbonates such as propylene carbonate, n-methyl pyrrolidone, ethers, esters, acetate and mixtures of any of the above.

Block copolymers may be prepared by the Group Transfer Polymerization ("GTP") process taught in U.S. Pat. No. 4,417,034, the disclosure of which is incorporated herein by reference.

Branch and graft copolymers comprise a backbone portion and one or more arms or side chains attached at a terminal end to the backbone. Such polymers have a "T" shape when only one arm is present and have a comb shape when more than one arm is present. Branch and graft copolymers can be prepared by polymerizing macromonomers to a polymer backbone. To ensure that the macromonomer only has one terminal ethylenically unsaturated group which will polymerize with the backbone monomers to form the copolymer, the macromonomer is polymerized by using a catalytic chain transfer agent that contains $Co^{+2}$ group, i.e., a cobalt chain transfer agent. Typically, in the first step of the process for preparing the macromonomer, the monomers are blended with a cobalt chain transfer agent and an inert organic solvent which is water miscible or water dispersible. The mixture is then heated, usually to the reflux temperature of the reaction mixture. In subsequent steps, additional monomers and cobalt catalyst and conventional azo-type polymerization catalyst, such as 2,2'-azobis(2-methylbutanenitrile) and 2,2'-azobis(2,4'-dimethylpentanenitrile) 2,2'-azobis(2,4-dimethyl-4-methoxyvaleronitrile), are added and polymerization is continued until a macromonomer is formed of the desired molecular weight.

Preferred cobalt chain transfer agents or catalysts are described in U.S. Pat. Nos. 4,680,352 and 4,722,984. Most preferred are pentacyanocobaltate (II), diaquabis (borondifluorodimethyl-glyoximate) cobaltate(II) and diaquabis(borondifluorophenylglyoximate) cobaltate (II). Typically these chain transfer agents are used at concentrations of about 5–1000 ppm based on the monomers used.

After the macromonomer is formed as described above, optionally solvent is stripped off and the backbone monomers are added to the macromonomer along with additional solvent and polymerization catalyst. Any of the aforementioned azo-type catalyst can be used, as can other suitable catalyst such as peroxides and hydroperoxides. Typical of such catalyst are di-tertiarybutyl peroxide, di-cumylperoxide, tertiaryamyl peroxide, cumenehydroperoxide, di(n-propyl) peroxy-dicarbonate, peresters such as amyl peroxyacetate, and the like. Polymerization is continued usually at the reflux temperature of the reaction mixture until a branch or graft copolymer is formed of the desired molecular weight.

Typical solvents that can be used to form the macromonomer or the graft copolymer are ketones such as methyl ethyl ketone, isobutyl ketone, ethyl amyl ketone, acetone, alcohols such as methanol, ethanol, isopropanol, esters such as ethyl acetate, glycols such as ethylene glycol, propylene glycol mono butyl ether, and the like.

The acrylic polymer dispersants will have a molecular weight (determined by gel permeation chromatography using polymethyl methacrylate as the standard) in the range of 5,000–200,000 daltons, most preferably in the range of 5,000–50,000 daltons. Acceptable glass transition temperatures ("Tg") for the acrylic dispersants are in the range of −20° C. to 140° C. Glass transition temperature of the polymer is measured by differential scanning calorimetry ("DSC").

The acrylic dispersants need to be soluble in the solvent system for the composition which, as stated above, is no more than 30% water, preferably no more than 5% water by weight. Accordingly, the acrylic polymer should contain 0–40% by weight acid monomers, preferably no more than 10% by weight of acid monomers, and the acid monomers should not be neutralized.

Particularly preferred acrylic polymer dispersants are those prepared from the same monomers and monomer combinations as the preferred acrylic polymer binders, discussed below.

In preparing the colored nail polish compositions of this invention, it will be desirable to make a pigment dispersion by mixing together the pigment(s) and the dispersant in the presence of a solvent under conditions of high shear to deflocculate the pigment and form an intimate mixture of pigment and dispersant. Typical dispersing apparatus used for this purpose include media mills (e.g., ball mills, sand mills), two-roll mills, three-roll mills, liquid jet interaction chambers (e.g., Microfluidizer® from Microfluidics Corporation), ultrasonic milling, etc., all of which are suitable.

Binders

Binders are film forming polymers that are used in nail polish compositions to provide desirable properties such as adhesion, hardness, gloss and the like. Binders useful in the compositions of this invention include acrylic binders and non-acrylic binders, with acrylic binders again being preferred.

Useful non-acrylic binders include cellulosic film formers such as nitrocellulose, cellulose acetate isobutyrate, cellulose acetate propionate, ethyl cellulose, vinyl polymers (e.g. polyvinyl acetate and polyvinyl alcohol), toluene sulfonamideformaldehyde condensates (Santolite MHP and/or Santolite MS-80); sucrose benzoate; sucrose acetate isobutyrate, copolymeric mixtures thereof, alkyds, polyesters, urethane polymers, formaldehyde condensates, nylon, Rosin resins, and cyclohexahones.

Particularly preferred are acrylic binders comprising copolymers of 60–99% by weight of (meth)acrylic acids, esters of (meth)acrylic acids, stirene and combinations thereof, wherein the binder further contains 1–40%, preferably 5–40% and most preferably 5–30% by weight, of adhesion promoting monomers (or monomer combinations) selected from the group consisting of (1) anhydride monomers, anhydride monomers with acid monomers, anhydride monomers in combination with ureido monomers, and anhydride monomers with beta-diketone monomers; (2) acid monomers in combination with hydroxy monomers; (3) ureido monomers, ureido monomers in combination with beta-diketone monomers, and ureido monomers in combination with acid monomers.

The structure of the acrylic polymer binders is not critical. Accordingly, random, block and branched or graft polymers are suitable. Such polymers can be prepared by a conventional solution polymerization process (random polymers), the GTP method (block polymers) or through the use of chain transfer agents (branch and graft polymers) discussed above.

The acrylic polymer contains 1–40% by weight of polymerized adhesion promoting monomers (or monomer combinations) selected from:

(1) anhydride monomers, anhydride monomers with acid monomers, anhydride monomers in combination with ureido monomers, and anhydride monomers with beta-diketone monomers;

(2) acid monomers in combination with hydroxy monomers; and (3) ureido monomers, ureido monomers in combination with beta-diketone monomers, and ureido monomers in combination with acid monomers.

Anhydride monomers and ureido monomers are considered to be primary adhesion monomers because they provide adequate adhesion by themselves. The hydroxy monomers, beta-diketone monomers and the acid monomers are considered to be secondary adhesion monomers because, by themselves they do not provide adequate adhesion, but appear to enhance the adhesion properties of the binders when used in combination with the primary monomers. Special mention needs to be made of the hydroxy monomers, which are suitable for use only in connection with acid monomers. For further clarification, the preferred binders of this invention contain the adhesion promoting monomers and monomer combinations identified with an "X" in the chart below:

|           | Acid | Ureido | Hydroxy | Anhydride | β-diketone |
|-----------|------|--------|---------|-----------|------------|
| Acid      |      | X      | X       | X         |            |
| Ureido    | X    | X      |         | X         | X          |
| Hydroxy   | X    |        |         |           |            |
| Anhydride | X    | X      |         | X         | X          |
| β-diketone|      | X      |         | X         |            |

Suitable anhydride monomers include maleic anyhdride, itaconic anhydride and half-esters thereof. Maleic anhydride monomers, including stirene maleic anhydride, are particularly preferred.

The β-diketone monomers suitable for use are those having structure (I):

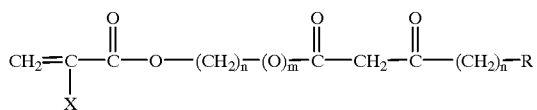

where X=CH₃ or H; n=1–10; m=0 or 1; and R=H or an organic moiety.

Suitable ureido monomers are those having structure (II):

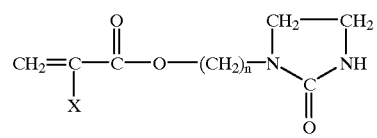

where X=CH₃ or H; and n=1–10. Some suitable β-diketone and ureido monomers include acetoacetoxyethyl methacrylate, 2-(acetoacetoxy)ethyl acrylate, methacrylamidoethylacetoxy acetate, hexadione methacrylate, 2-(acetoacetoxy) propyl methacrylate, N-(2-methacryloyloxyethyl)ethylene urea, and methacrylamidoethylethylene urea.

Suitable hydroxy monomers include hydroxy alkyl (meth) acrylates having 1–4 carbon atoms in the alkyl group such as hydroxyethyl methacrylate, hydroxycthyl acrylate, hydroxypropyl methacrylate, hydroxypropyl acrylate, hydroxybutyl methacrylate and hydroxybutyl acrylate. In addition, those skilled in the art will appreciate that monomers such as vinyl acetate may be employed and readily hydrolyzed to form free OH groups.

Apart from the adhesion promoting monomers, the preferred acrylic polymer binders are prepared from (meth) acrylic acid monomers, esters of (meth)acrylic acid monomers, and stirene monomers. Particularly preferred are alkyl (meth)acrylates having 1–12 carbons in the alkyl group, aryl (meth)acrylates, cylic (meth)acrylates and alicyclic (meth)acrylates. Examples of useful monomers include methyl acrylate, methyl methacrylate, stirene, alpha-methyl stirene, phenyl acrylate, phenyl methacrylate, benzyl acrylate, benzyl methacrylate, 2-phenylethyl acrylate, 2-phenylethyl methacrylate, 2-phenoxyethyl acrylate, 2-phenoxyethyl methacrylate, 1-napthalyl acrylate, 2-napbthalyl acrylate, 2-napbthalyl methacrylate, p-nitrophenyl acrylate, p-nitrophenyl methacrylate, phthalimidomethyl acrylate, phthalimidomethyl methacrylate, N-phenyl acrylamide, N-phenyl methacrylamide, N-benzyl acrylamide, N-(2-phenylethyl)acrylamide, N-(2-phthalimidoethoxymethyl) acrylamide, ethyl acrylate, n-butyl acrylate, 2-ethylhexyl acrylate, ethyl methacrylate, n-butyl methacrylate, t-butyl methacrylate, 2-ethylhexyl methacrylate, cyclohexyl methacrylate, t-butylaminoethyl methacrylate, dimethylaminoethyl methacrylate, isobutyl methacrylate, hexyl methacrylate, 2-ethyl hexyl methacrylate, nonyl methacrylate, lauryl methacrylate, hexyl acrylate, 2-ethyl hexyl acrylate, nonyl acrylate, lauryl acrylate and the like; isobornyl methacrylate, isobornyl acrylate, cyclohexyl methacrylate, cyclohexyl acrylate, ethoxy tri ethylene glycol methacrylate and ethoxy triethylene glycol acrylate, acrylamide, methacrylamide, and mixtures of any of these monomers.

Particularly preferred acrylic polymer binders are:
  butyl methacrylate (70–80 wt. %), maleic anhydride (10–20 wt. %) and acrylic acid (10 wt %);
  butyl acrylate (5 wt %), butyl methacrylate (65 wt %), maleic anhydride (20 wt %) and acrylic acid (10 wt %); and
  methyl methacrylate (10–40 wt %), butyl methacrylate (30–60 wt %), maleic anhydride (20 wt %) and acrylic acid (10 wt %)

The acrylic polymer binders have a weight average molecular weight of 10,000–3,000,000, preferably 10,000 to 200,000 and most preferably between 20,000 and 120,000 and a glass transition temperature ("Tg") of 0–140° C., preferably 20–120° C. and most preferably 40–80° C.

Other Ingredients

The compositions of the invention may also contain other ingredients commonly used in nail polish compositions, such as emulsifiers, humectants, ancillary film formers, defoamers, plasticizers, preservatives, UV light absorbers, stabilizer, fragrances, moisturizers and the like.

Plasticizers are perhaps the most commonly used additive in nail polish compositions. If used in the present compositions, the plasticizer may be in either liquid or solid form, as well as combinations thereof. Examples of known plasticizers include tricresyl phosphate, dibutyl tartrate, benzyl benzoate, tributyl phosphate, butyl acetyl ricinoleate, glyceryl acetyl ricinoleate, butyl glycolate, butyl stearate, triphenyl phosphate, triethyl citrate, camphor, castor oil, esters of citric, stearate, phthalic, oleic, phosphate, butyric and benzoic acid (e.g., dibutyl phthalate, dioctyl phthalate, butyl stearate, tributoxyethyl phosphate, triphenyl phosphate, tributyl citrate, tributyl acetylcitrate, tri-2-ethylhexyl acetylcitrate, dimethoxyethyl phthalate, diisobutyl phthalate, diamyl phthalate), glyceryl triacetate and glyceryl triproprionate and mixtures thereof.

Plasticizers included in the compositions of the present invention are in amounts sufficient to provide acceptable flexibility to the nail polish film on the human or synthetic nail surface. In this regard, the amount of plasticizer for use in the nail polish compositions of the present invention range from about 3 to 10% by weight, and preferably about 4 to 8% by weight.

It may also be desirable to include 0.1–20% by weight of the total composition, of a silicone glycol copolymer in the composition. Silicone glycol copolymers which may be used in the compositions of the invention are polymethylsiloxanes wherein a portion of the methylsiloxane units are substituted with polyalkylene glycol ether moieties. Preferred is wherein about 60–90% of the polymer (the percentage being based on the number of monomer units), of the compound is polydimethylsiloxane or polyhydrogen methylsiloxane and 30–40% of the compound (the percentage being based upon the number of monomer units) is di-methyl or hydrogen-methyl siloxane units substituted with polyalkylene glycol ethers. Most preferred are silicone glycol copolymers having a viscosity ranging from 1.0 to 500,000, preferably 1.0 to 2,000 centipoise at 25° C., a specific gravity ranging from 0.80 to 1.030 at 25° C., and comprise approximately 80% dimethylsiloxane units and 20% propylene oxide substituted methyl siloxane units. Silicone glycol copolymers having this description are commercially available from a variety of sources including Dow Coming under the trade names Dow Coming Additive 3, 7, 11, 14, 18,21,24,26,28,29,51, 54,56,57, and 1248.

EXAMPLES

The following are examples which illustrate the invention. All parts and percentages are on a weight basis unless otherwise specified.

Example 1

A series of dispersions were prepared by mixing together a pigment, a dispersant, dibutylphthalate plasticizer and butyl acetate solvent and milling the mixture in an attritor containing ceramic beads (120S-0.8–1.0 mm from SEPR Co) grinding media until a homogeneous dispersion was obtained. The compositions of the dispersions are set forth in Table 1. The amounts in the table are expressed in grams.

TABLE 1

| Dispersion No. | Pigment | | | | Dispersant | | |
|---|---|---|---|---|---|---|---|
| | $TiO_2$[1] | Red $Fe_2O_3$[2] | Red Lake#6[3] | Bentonite Clay | Cellulose Nitrate[4] | Acrylic Polymer[5] | Butyl Acetate |
| 1 | 240 | | | | 50 | | 126.7 |
| 2 | | 75 | | | 187.5 | | 331.25 |
| 3 | | | 90 | | 225 | | 185 |
| 4 | | | | 25 | 475 | | — |
| 5 | 240 | | | | | 25 | 151.7 |
| 6 | | 75 | | | | 93.75 | 331.25 |
| 7 | | | 90 | | | 112.5 | 207.5 |
| 8 | | | | 25 | | 237.5 | 157.5[6] |

Notes to Table 1:
[1]·R960 titanium dioxide pigment from DuPont.
[2]·Red iron oxide pigment from Warner Jenkinson Co
[3]·From Sun Chemical Co.
[4]·20% solution of 80/20 mixture of cellulose nitrate from Aldrich Co. (11% nitrogen content, 30–35 cps viscosity)/dibutylphthalate in butyl acetate and isopropanol solvents.
[5]·40% solution of butylmethacrylate-co-methylmethacrylate-co-acrylic acid (20/70/10 wt. %) in butyl acetate and ethyl acetate solvents.
[6]·80 gms of isopropanol was also added.

Two nail polish compositions were then prepared from the above dispersions. In the first nail polish composition, the nitrocellulose dispersions (0.1275 gms of Dispersion #1; 0.75 gms of Dispersion #2; 6.6 gms of Dispersion #3; and 3.0 gms of Dispersion #4) were mixed with 140 grams of 20% solution of 80/20 mixture of cellulose nitrate (from Aldrich Co, 11% nitrogen content, 30–35 cP viscosity)/ dibutylphthalate in butyl acetate and isopropanol solvents to form a homogeneous mixture. In the second nail polish composition, the acrylic dispersions (0.1275 gms of Dispersion #5; 0.75 gms of Dispersion #6; 6.6 gms of Dispersion #7; and 3.0 gms of Dispersion #8) were mixed with 70 grams of 40% solution of butylmethacrylate-co-methylmethacrylate-co-acrylic acid (20/70/10 wt. %) in butyl acetate and ethyl acetate solvents and 70 grams of butyl cellosolve.

The nail polish compositions from above were drawn-down (6 mil clearance) on glass and their drying characteristics, hardness, and gloss development were evaluated under the following test procedures:

Cotton Ball Dry Time: A cotton swab or cotton ball is lightly drawn over the film surface. The time in seconds or minutes reported is that period after which no streaks or striations are formed on the film surface.

Zapon Tack Free: The film tack time is measured using a Zapon(O Tack Tester from Lanchem Corporation.

Gloss: Measured value using a ProGloss(® meter from Hunter Labs.

Fisher Hardness: Indentation hardness measurement using a Fisherscope Hardness instrument from Fisher Scientific. Units are Newtons per square meter.

Cross Hatch Adhesion: A conventional coatings adhesion test described in R. R. Myers & T. S. Long, Treatise on Coatings, Vol. 2, Part 1, page 73 (1969). The results are shown in Table 3.

TABLE 3

| Property | | Nail Polish Composition | |
|---|---|---|---|
| | | 1 | 2 |
| Cotton Ball Dry Time | | 14:20 | 11:45 |
| Zapon Tack Free | | 17:00 | 15:00 |
| Gloss (60°) | @ 0.5 hr | 87.9 | 85.1 |
| | @ 24 hr | 89.9 | 91.2 |
| | @ 96 hr. | 92.9 | 88.5 |
| Fisher Hardness | @ 0.5 hr | 66 | 47 |
| | @ 1 hr | 93 | 75 |
| | @ 2 hr | 110 | 93 |
| | @ 4 hr | 124 | 98 |
| | @ 24 hr | 155 | 132 |
| | @ 96 hr | 147 | 139 |

Example 2

A series of acrylic polymer binders containing the adhesion promoting monomers and monomers combinations noted above were prepared and used to formulate nail polish compositions. The polymer preparation is described first followed by the nail polish formulation and test data.

Polymer A: Stirene-co-butyl methacrylate-co-maleic anhydride-co-methyl methacrylate (5/35/10/50 wt %)

To a 2 liter flask fitted with reflux condenser, addition pumps, agitator and heating mantle is added 165.1 gms of ethyl acetate and 71.5 gms butyl acetate. The solvent mixture is agitated and the temperature raised to reflux (85 to 95° C.). A mixture of 23.3 gms stirene, 153.1 gms n-butyl methacrylate, 46.6 gms maleic anhydride, 233.0 gms methyl methacrylate and 66.0 gms ethyl acetate is fed over 90 minutes simultaneously with a mixture of 70.4 gms butyl acetate, 264.1 gms ethyl acetate and 8.8 gms of 2,2-azobis-(2,4-dimethyl) valeronitrile (Vazo® 52, DuPont) which is fed over 360 minutes while maintaining agitation and reflux and conditions. The monomer feed, when complete, is followed by the addition of 11.0 gms ethyl acetate and 11.0 gms of butyl acetate over 5 minutes and the initiator feed, when complete, is followed by the addition of 66.0 gms ethyl acetate over 5 minutes. The reaction mixture is held at reflux for 90 minutes following completion of the initiator feed and then cooled to room temperature. The resulting copolymer solution is 39.3 wt. % solids with a viscosity of 400 cps as measured by a Brookfield viscometer at 5 rpm/spindle #3. Molecular weights measured via gel permeation chromatography ("GPC") with polystyrene as standard are: number average 15423 and weight average 46100. The Tg as measured by DSC is 64° C.

Polymer B: Stirene-co-butyl methacrylate-co-maleic anhydride-co-methyl methacrylate (5/20/10/65 wt %)

To a 2 liter flask fitted with reflux condenser, addition pumps, agitator and heating mantle is added 165.1 gms of ethyl acetate and 71.5 gms butyl acetate. The solvent mixture is agitated and the temperature raised to reflux (85 to 95° C.). A mixture of 23.3 gms stirene, 93.2 grns n-butyl methacrylate, 46.6 gms maleic ahhydride, 302.9 gms methyl methacrylate and 66.0 gms ethyl acetate is fed over 90 minutes simultaneously with a mixture of 70.4 gms butyl acetate, 264.1 gms ethyl acetate and 8.8 gms Vazo® 52 which is fed over 360 minutes while maintaining agitation and reflux conditions. The monomer feed, when complete, is followed by the addition of 11.0 gms ethyl acetate and 11.0 gms of butyl acetate over 5 minutes and the initiator feed, when complete, is followed by the addition of 66.0 gms ethyl acetate over 5 minutes. The reaction mixture is held at reflux for 90 minutes following completion of the initiator feed and then cooled to room temperature. The resulting copolymer solution is 38.7 wt % solids with a viscosity of 660 cps as measured by a Brookfield viscometer at 5 rpm/spindle #3. Molecular weights measured via GPC with polystyrene as standard are: number average 14712 and weight average 46218. The Tg as measured by DSC is 67° C.

Polymer C: Stirene-co-butyl methacrylate-co-maleic anhydride-co-methyl methacrylate-co-acetoacetoxyethyl methacrylate (5/25/10/50/10 wt %)

To a 2 liter flask fitted with reflux condenser, addition pumps, agitator and heating mantle is added 165.1 gms of ethyl acetate and 71.5 gms butyl acetate. The solvent mixture is agitated and the temperature raised to reflux (85 to 95° C.). A mixture of 23.3 gms stirene, 116.5 gms n-butyl methacrylate, 46.6 gms maleic anhydride, 233.0 gms methyl methacrylate, 46.6 gms acetoacetoxyethyl methacrylate and 66.0 gms ethyl acetate is fed over 90 minutes simultaneously with a mixture of 70.4 gms butyl acetate, 264.1 gms ethyl acetate and 8.8 gms Vazo® 52 which is fed over 360 minutes, while maintaining agitation and reflux conditions. The monomer feed, when complete, is followed by the addition of 11.0 gms ethyl acetate and 1 1.0 gms of butyl acetate over 5 minutes and the initiator feed, when complete, is followed by the addition of 66.0 gms ethyl acetate over 5 minutes. The reaction mixture is held at reflux for 90 minutes following completion of the initiator feed and then cooled to room temperature. The resulting copolymer solution is 37 wt % solids with a viscosity of 408 cps as measured by a Brookfield viscometer at 5 rpm/spindle #3. Molecular weights measured via GPC with polystyrene as standard are: number average 12260 and weight average 44358. The Tg as measured by DSC is 69° C.

Polymer D: Stirene-co-butyl methacrylate-co-maleic anhydride-co-methyl methacrylate-co-acrylic acid (5/35/8/50/2 wt %)

To a 2 liter flask fitted with reflux condenser, addition pumps, agitator and heating mantle is added 165.1 gms of ethyl acetate and 71.5 gms butyl acetate. The solvent mixture is agitated and the temperature raised to reflux (85 to 95° C.). A mixture of 23.3 gms stirene, 163.1 gms n-butyl methacrylate, 37.3 gms maleic anhydride, 233.0 gms methyl methacrylate, 9.3 gms acrylic acid and 66.0 gms ethyl acetate is fed over 90 minutes simultaneously with a mixture of 70.4 gms butyl acetate, 264.1 gms ethyl acetate and 8.8 gms Vazo® 52 which is fed over 360 minutes while maintaining agitation and reflux conditions. The monomer feed, when complete, is followed by the addition of 11.0 gms ethyl acetate and 11.0 gms of butyl acetate over 5 minutes and the initiator feed, when complete, is followed by the addition of 66.0 gms ethyl acetate over 5 minutes. The reaction mixture is held at reflux for 90 minutes following completion of the initiator feed and then cooled to room temperature. Weight solids of the resulting copolymer solution is 37.1% with a viscosity of 420 cps as measured by a Brookfield viscometer at 5 rpm/spindle #3. Molecular weights measured via GPC with polystyrene as standard are: number average 14961 and weight average 46362. The Tg as measured by DSC is 66° C.

Polymer E: Stirene-co-butyl methacrylate-co-maleic anhydride-co-methyl methacrylate-co-acetoacetoxyethyl methacrylate (7.5/70/10/7.5/5 wt %)

To a 2 liter flask fitted with reflux condenser, addition pumps, agitator and heating mantle is added 158.8gms of ethyl acetate and 68.1gms butyl acetate. The solvent mixture is agitated and the temperature raised to reflux (86 to 94° C.). A mixture of 36.0 gms stirene, 336.2 gms n-butyl methacrylate, 48.0 gms maleic anhydride, 36.0 gms methyl methacrylate, 24.0 gms acetoacetoxyethyl methacrylate and 11.3 gms ethyl acetate is fed over 150 minutes simultaneously with a mixture of 28.4 gms butyl acetate, 136.1 gms ethyl acetate and 5.1 gms Vazog 52 which is fed over 360 minutes while maintaining agitation and reflux conditions. The monomer feed, when complete, is followed by the addition of 11.3 gms ethyl acetate and 22.7 gms of butyl acetate over 5 minutes and the initiator feed, when complete, is followed by the addition of 249.6 gms ethyl acetate and 28.4 gms butyl acetate over 5 minutes. The reaction mixture is held at reflux for 90 minutes following completion of the initiator feed and then cooled to room temperature. Weight solids of the resulting copolymer solution is 39.5% with a viscosity of 272 cps as measured by a Brookfield viscometer at 5 rpm/spindle #3. Molecular weights measured via GPC with polystyrene as standard are: number average 20879 and weight average 59804. The Tg as measured by DSC is 58° C.

Polymer F: Stirene-co-butyl methacrylate-co-maleic anhydride-co-methyl methacrylate-co-acetoacetoxyethyl methacrylate (5/25/10/40/20 wt %)

To a 2 liter flask fitted with reflux condenser, addition pumps, agitator and heating mantle is added 165.6 gms of ethyl acetate and 71.7 gms butyl acetate. The solvent mixture is agitated and the temperature raised to reflux (86 to 94° C.). A mixture of 23.4 gms stirene, 116.8 gms n-butyl methacrylate, 46.7 gms malcic anhydride, 186.7 gms methyl methacrylate, 93.5 gms acetoacetoxyethyl methacrylate and 11.0 gms ethyl acetate is fed over 120 minutes simultaneously with a mixture of 48.6 gms butyl acetate, 176.6 gms ethyl acetate and 5.5 gms Vazo® 52 which is fed over 360 minutes while maintaining agitation and reflux conditions.

The monomer feed, when complete, is followed by the addition of 11.0 gms ethyl acetate and 11.0 gms of butyl acetate over 5 minutes and the initiator feed, when complete, is followed by the addition of 209.7 gms ethyl acetate and 22.0 gms butyl acetate over 5 minutes. The reaction mixture is held at reflux for 90 minutes following completion of the initiator feed and then cooled to room temperature. Weight solids of the resulting copolymer solution is 39.4% with a viscosity of 816 cps as measured by a Brookfield viscometer at 5 rpm/spindle #3. Molecular weights measured via GPC with polystirene as standard are: number average 21941 and weicht average 67398. The Tg as measured by DSC is 72° C.

Polymer G: Stirene-co-butyl methaerylate-co-maleic anhydride-co-methyl methacrylate-co-acetoacetoxyethyl methacrylate (10/25/15/40/10 wt %)

To a 2 liter flask fitted with reflux condenser, addition pumps, agitator and heating mantle is added 165.6 gms of ethyl acetate and 71.7 gms butyl acetate. The solvent mixture is agitated and the temperature raised to reflux (86 to 94° C.). A mixture of 46.7 gms stirene, 11 6.8 gms n-butyl methacrylate, 70.1 gms maleic anhydride, 186.7 gms methyl methacrylate, 46.7 gms acetoacetoxyethyl methacrylate and 11.0 gms ethyl acetate is fed over 120 minutes simultaneously with a mixture of 48.6 gms butyl acetate, 176.6 gms ethyl acetate and 5.5 gms Vazo® 52 which is fed over 360 minutes while maintaining agitation and reflux conditions. The monomer feed, when complete, is followed by the addition of 11.0 gms ethyl acetate and 11.0 gms of butyl acetate over 5 minutes and the initiator feed, when complete, is followed by the addition of 209.7 gms ethyl acetate and 22.0 gms butyl acetate over 5 minutes. The reaction mixture is held at reflux for 90 minutes following completion of the initiator feed and then cooled to room temperature. Weight solids of the resulting copolymer solution is 38.3% with a viscosity of 1112 cps as measured by a Brookfield viscometer at 5 rpm/spindle #3. Molecular weights measured via GPC with polystyrene as standard are: number average 21395 and weight average 66698. The Tg as measured by DSC is 75° C.

Polymer H: Stirene-co-butyl methacrylate-co-N-(2-methacryloxyloxyethyl-2-ethylene urea)-co-methyl methacrylate-co-acetoacetoxyethyl methacrylate (5/70/5/1515 wt %)

To a 2 liter flask fitted with reflux condenser, addition pumps, agitator and heating mantle is added 171.8 gms of ethyl acetate and 74.4 gms butyl acetate. The solvent mixture is agitated and the temperature raised to reflux (86 to 94° C.). A mixture of 23.3 gms stirene, 339.4 gms n-butyl methacrylate, 97.9 gms of a 25% solution of N-(2methacryloyloxyethy-2-ethylene urea) in methyl methacrylate, 24.2 gms acetoacetoxyethyl methacrylate and 11.5 gms ethyl acetate is fed over 90 minutes simultaneously with a mixture of 50.4 gms butyl acetate, 183.2 gms ethyl acetate and 4.0 gms Vazo® 52 which is fed over 360 minutes while maintaining agitation and reflux conditions. The monomer feed, when complete, is followed by the addition of 5.7 gms ethyl acetate and 5.7 gms of butyl acetate over 5 minutes and the initiator feed, when complete, is followed by the addition of 194.7 gms ethyl acetate and 13.7 gms butyl acetate over 5 minutes. The reaction mixture is held at reflux for 90 minutes following completion of the initiator feed and then cooled to room temperature. Weight solids of the resulting copolymer solution is 39.3% with a viscosity of 380 cps as measured by a Brookfield viscometer at 5 rpm/spindle #3. Molecular weights measured via GPC with polystirene as standard are: number average 28812 and weight average 96313. The Tg as measured by DSC is 60° C.

Polymer I: Stirene-co-butyl methaerylate-co-N-(2-methacryloyloxyethy-2-ethylene urea)-co-methyl methaerylate-co-acetoacetoxyethyl methacrylate (5/45/5/40/5 wt %)

To a 2 liter flask fitted with reflux condenser, addition pumps, agitator and heating mantle is added 171.8 gms of ethyl acetate and 74.4 gms butyl acetate. The solvent mixture is agitated and the temperature raised to reflux (86 to 94° C.). A mixture of 23.3 gms stirene, 219.2 gms n-butyl methacrylate, 97.9 gms of a 25% solution of N-(2methacryloyloxyethy-2-ethylene urea) in methyl methacrylate, 120.2 gms methyl methacrylate, 24.2 gms acetoacetoxyethyl methacrylate and 11.5 gms ethyl acetate is fed over 90 minutes simultaneously with a mixture of 50.4 gms butyl acetate, 183.2 gms ethyl acetate and 4.0 gms Vazo® 52 which is fed over 360 minutes while maintaining agitation and reflux conditions. The monomer feed, when complete, is followed by the addition of 5.7 gms ethyl acetate and 5.7 gms of butyl acetate over 5 minutes and the initiator feed, when complete, is followed by the addition of 194.7 gms ethyl acetate and 13.7 gms butyl acetate over 5 minutes. The reaction mixture is held at reflux for 90 minutes following completion of the initiator feed and then cooled to room temperature. Weight solids of the resulting copolymer solution is 40.2% with a viscosity of 1300 cps as measured by a Brookfield viscometer at 5 rpm/spindle #3. Molecular weights measured via GPC with polystirene as standard are: number average 28569 and weight average 89094. The Tg as measu red by DSC is 70.C.

Polymer J: Butyl methacrylate-co-N-(2-m ethaeryloyloxyethy-2-ethylene urea-co-methyl methacrylate-co-acrylic acid (35/10/5015 wt %)

To a 2 liter flask fitted with reflux condenser, addition pumps, agitator and heating mantle is added 170.1 gms of ethyl acetate and 73.7 gms butyl acetate. The solvent mixture is agitated and the temperature raised to reflux (86 to 94° C.). A mixture of 24.0 gms acrylic acid, 166.0 gms n-butyl methacrylate, 193.3 gms of a 25% solution of N-(2methacryloyloxyethy-2-ethylene urea) in methyl methacrylate, 96.8 gms methyl methacrylate and 11.3 gms ethyl acetate is fed over 90 minutes simultaneously with a mixture of 68.0 gms butyl acetate, 317.5 gms ethyl acetate and 5.7 gms Vazo® 52 which is fed over 360 minutes while maintaining agitation and reflux conditions. The monomer feed, when complete, is followed by the addition of 5.7 gms ethyl acetate and 5.7 gms of butyl acetate over 5 minutes and the initiator feed, when complete, is followed by the addition of 62.4 gms ethyl acetate over 5 minutes. The reaction mixture is held at reflux for 90 minutes following completion of the initiator feed and then cooled to room temperature. Weight solids of the resulting copolymer solution is 38.0% with a viscosity of 8640 cps as measured by a Brookfield viscometer at a rpm/spindle 33. Molecular weights measured via GPC with polystyrene as standard are: number average 24457 and weight average 84571. The Tg as measured by DSC is 64° C.

Polymer K: Butyl methacrylate-co-hydroxyethyl meth acrylate-co-acrylic acid (70/20/1 0 wt %)

To a 2 liter flask fitted with reflux condenser, addition pumps, agitator and heating mantle is added 264.2 gms of ethyl acetate and 118.5 gms butyl acetate. The solvent mixture is agitated and the temperature raised to reflux (85 to 92° C.). A mixture of 60.1 gms acrylic acid, 420.6 gms n-butyl methacrylate, 120.2 gms hydroxyethyl methacrylate and 14.2 gms ethyl acetate is fed over 180 minutes s imultaneously with a mixture of 132.2 gms ethyl acetate and 8.4 gms Vazo® 52 which is fed over 360 minutes while maintaining agitation and reflux conditions. The monomer feed, when complete, is followed by the addition of 14.2 gms ethyl acetate over 5 minutes and the initiator feed, when complete, is followed by the addition of 5.0 gms ethyl acetate over 5 minutes. The reaction mixture is held at reflux for 20 minutes following completion of the initiator feed, 42.6 gms ethyl acetate are added and the reaction mixture cooled to room temperature. Weight solids of the resulting copolymer solution is 50.9% with a viscosity of 10400 cps as measured by a Brookfield viscometer at 5 rpm/spindle #3. Molecular weights measured via GPC with polystyrene as standard are: number average 23570 and weight average 68250. The Tg as measured by DSC is 56° C.

Polymer M: Hydroxyethyl methacrylate-co-methyl methacrylate (20/80 wt. %)

To a 2 liter flask fitted with reflux condenser, addition pumps, agitator and heating mantle is added 362.3 gms of ethyl acetate and 149.2 gms butyl acetate. The solvent mixture is agitated and the temperature raised to reflux (85 to 92° C.). A mixture of 361 gms methyl methacrylate, 90.2 gms hydroxyethyl methacrylate and 10.7 gms ethyl acetate is fed over 180 minutes simultaneously with a mixture of 99.3 g-ns ethyl acetate and 6.3 gms Vazo® 52 which is fed over 360 minutes while maintaining agitation and reflux conditions. The monomer feed, when complete, is followed by the addition of 85.3 gnms ethyl acetate and 10.7 gims butyl acetate over 5 minutes and the initiator feed, when complete, is followed by the addition of 3.8 gms ethyl acetate over 5 minutes. The reaction mixture is held at reflux for 20 minutes following completion of the initiator feed, 21.3 gms ethyl acetate are added and the reaction mixture cooled to room temperature. Weight solids of the resulting copolymer solution is 34.9% with a viscosity of 2360 cps as measured by a Brookfield viscometer at 5 rpm/spindle #3. Molecular weights measured via GPC with polystyrene as standard are: number average 14330 and weight average 33220. The Tg as measured by DSC is 90° C.

Formulations and Testing

A series of nail polish formulations were prepared using the above polymers either alone or plasticized with either butyl benzyl phthalate ("BBP", Santicizer® 160 from Solutia Corp.) or tri-tolyl phosphate ("TTP", RB6 from Roland Corp.). The plasticizer to polymer weight ratio was 10 to 90 in all cases. For comparison purposes, two commercial "FAST DRY" nail polish compositions —L'Oreal Jet Set 250 ("Comparative A") and Maybelline 350 ("Comparative B")—were subjected to the same test procedures. All compositions were tested for dry time, gloss, adhesions and hardness using the procedures described above. Results are reported in Table 4.

TABLE 4

| Polymer | Plasticizer | Cotton Ball Dry (sec.) | 20° Gloss 24 hr. | Cross Hatch Adhesion | | Fisher Hardness | |
|---|---|---|---|---|---|---|---|
| | | | | 4 hr. | 24 hr. | 4 hr. | 24 hr. |
| A | BBP | 90 | 162 | 9 | 7 | 53 | 81 |
| B | TTP | 55 | 163 | 8 | 8 | 67 | 90 |
| C | BBP | 97 | 164 | 9 | 8 | 49 | 79 |
| D | BBP | 97 | 148 | 9 | 7 | 42 | 73 |
| E | TTP | 170 | 155 | 10 | 10 | 18 | 42 |
| F | TTP | 150 | 168 | 9 | 9 | 36 | 74 |
| F | | 105 | 154 | 9 | 10 | 84 | 108 |
| G | TTP | 120 | 160 | 8 | 8 | 73 | 95 |
| H | BBP | 190 | 166 | 10 | 10 | 6 | 10 |
| I | BBP | 130 | 160 | 10 | 9 | 15 | 40 |
| I | | 105 | 160 | 10 | 9 | 12 | 82 |

TABLE 4-continued

| Polymer | Plasticizer | Cotton Ball Dry (sec.) | 20° Gloss 24 hr. | Cross Hatch Adhesion | | Fisher Hardness | |
|---|---|---|---|---|---|---|---|
| | | | | 4 hr. | 24 hr. | 4 hr. | 24 hr. |
| J | BBP | 120 | 169 | 10 | 8 | 6 | 47 |
| K | BBP | 150 | 158 | 9 | 10 | 5 | 23 |
| L | BBP | 180 | 162 | 10 | 10 | 7 | 31 |
| M | | | | 6 | 6 | | 76 |
| Comp. Ex. A | | 260 | 50 | | | 42 | 45 |
| Comp. Ex. B | | 270 | 47 | | | 40 | 78 |

What is claimed is:

1. A nail polish composition comprising:
   a) a solvent system comprising at least one organic solvent; and
   b) a binder comprising an acrylic copolymer selected from the group consisting of:
      (i) butyl methacrylate (70–80 wt. %); maleic anhydride (10–20 wt. %) and acrylic acid (10 wt %);
      (ii) butyl acrylate (5 wt %), butyl methacrylate (65 wt %), maleic anhydride (20 wt %) and acrylic acid (10 wt %); and
      (iii) methyl methacrylate (10–40 wt %) butyl methacrylate (30–60 wt %), maleic anhydride (20 wt %) and acrylic acid (10 wt %).

2. The composition of claim 1 wherein the acrylic polymer binders have a weight average molecular weight between 20,000 and 120,000 and a glass transition temperature of 40–80° C.

3. A nail polish composition comprising:
   a) a solvent system comprising at least one organic solvent;
   b) a pigment;
   c) a polymeric dispersant comprising an acrylic polymer prepared from monomers selected from the group consisting of (meth)acrylic acid, esters of (meth)acrylic acid, and stirene; and
   d) a binder comprising copolymers of 60–95% by weight of (meth)acrylic acids esters of (meth)acrylic acids, stirene and combinations thereof, wherein the binder further contains 1–40% by weight of adhesion promoting monomers selected from the group consisting of:
      (i) anhydride monomers, anhydride monomers in combination with acid monomers, anhydride monomers in combination with ureido monomers, and anhydride monomers in combination with beta-diketone monomers;
      (ii) acid monomers in combination with hydroxy monomers; and
      (iii) ureido monomers, ureido monomers in combination with beta-diketone monomers, and ureido monomers in combination with acid monomers.

4. The nail polish composition of claim 3, wherein the acrylic polymer dispersant has a molecular weight of 5,000–50,000 and a glass transition temperature in the range of −20° C. to 140° C.

5. The composition of claim 3, wherein the acrylic binder has a weight average molecular weight between 20,000 and 120,000 and a glass transition temperature of 40–80° C.

6. A nail polish composition comprising:
   a) 20–95% by weight of the total nail polish composition of a solvent system having no more than 30% by weight water based on the weight of the solvent system, said solvent system comprising at least one organic solvent selected from the group consisting of acetone, diacetone alcohol, dihydroxyacetone, ethyl butyl valerolactone, methyl ethyl ketone, methanol, propanol, benzyl alcohol, butoxyethanol, butoxypropanol, butyl alcohol, 3-methyl-3-methoxybutanol, t-butyl alcohol, butylene glycol, diethylene glycol, abietyl alcohol, propylene carbonate, hexyl alcohol, isopropanol, butyl acetate, ethyl acetate, methyl acetate, propyl acetate, amyl acetate, pentane, cyclopentane, hexane, heptane, cyclohexane, tetrahydrofuran, 1,4-dioxane, cellosolve, butyl cellosolve acetate, cellosolve acetate, methyl cellosolve acetate, butyl cellosolve, ethyl cellosolve, xylene, methylene chloride, chloroform, methylchloroform and toluene;

b) 5–80% by weight of the total nail polish composition of an acrylic polymer binder having a weight average molecular weight between 20,000 and 120,000 and a glass transition temperature of 40–80° C., said binder comprising a copolymer of 60–95% by weight of (meth)acrylic acids, esters of (meth)acrylic acids, stirene and combinations thereof, wherein the binder further contains 1–40% by weight of adhesion promoting monomers selected from the group consisting of:
   (1) anhydride monomers, anhydride monomers in combination with acid monomers, anhydride monomers in combination with ureido monomers, and anhydride monomers in combination with beta-diketone monomers;
   (2) acid monomers in combination with hydroxy monomers; and
   (3) ureido monomers, ureido monomers in combination with beta-diketone monomers, and ureido monomers in combination with acid monomers;

c) 0.1–30% by weight based on the total weight of the composition of at least one pigment;

d) 0.1–15% by weight based on the total weight of the composition of an acrylic polymer dispersant having a molecular weight of 5,000–50,000 and a glass transition temperature in the range of –20° C. to 140° C., said dispersant comprising a copolymer of 60–95% by weight of (meth)acrylic acids, esters of (meth)acrylic acids, stirene and combinations thereof, wherein the binder further contains 1–40% by weight of adhesion promoting monomers selected from the group consisting of:
   (1) anhydride monomers, anhydride monomers in combination with acid monomers, anhydride monomers in combination with urcido monomers, and anhyd ride monomers in combination with beta-diketone monomers;
   (2) acid monomers in combination with hydroxy monomers; and
   (3) ureido monomers, ureido monomers in combination with beta-diketone monomers, and ureido monomers in combination with acid monomers; and e) 0–20% of the total weight of the composition of at least one additive selected from the group consisting of emulsifiers, humectants, ancillary film formers, defoamers, plasticizers, preservatives, UV light absorbers, stabilizer, fragrances, moisturizers, and silicon polymers.

* * * * *

UNITED STATES PATENT AND TRADEMARK OFFICE
CERTIFICATE OF CORRECTION

PATENT NO.    : 6,254,878 B1
DATED         : July 3, 2001
INVENTOR(S)   : Milan Bohuslav Bednarek et al.

It is certified that error appears in the above-identified patent and that said Letters Patent is hereby corrected as shown below:

<u>Title page,</u>
Item [57], ABSTRACT,
Line 4, "stirene" should be -- styrene --.

<u>Column 16,</u>
Line 39, "stirene" should be -- styrene --.
Line 42, "stirene" should be -- styrene --.

<u>Column 17,</u>
Line 22, "stirene" should be -- styrene --.

<u>Column 18,</u>
Line 10, "stirene" should be -- styrene --.

Signed and Sealed this

Fifth Day of November, 2002

*Attest:*

JAMES E. ROGAN
*Director of the United States Patent and Trademark Office*

*Attesting Officer*